(12) United States Patent
McKeon et al.

(10) Patent No.: US 8,932,236 B1
(45) Date of Patent: Jan. 13, 2015

(54) MONITORING POSTURE

(75) Inventors: Brian P. McKeon, Essex, MA (US); John D. Fiegener, Marblehead, MA (US); Daniel R. Armstrong, Marblehead, MA (US); Michael D. Tinstman, Revere, MA (US); Paul Demkowski, San Diego, CA (US)

(73) Assignee: Perseus Athletics, LLC, Essex, MA (US)

( * ) Notice: Subject to any disclaimer, the term of this patent is extended or adjusted under 35 U.S.C. 154(b) by 0 days.

(21) Appl. No.: 13/333,101

(22) Filed: Dec. 21, 2011

Related U.S. Application Data

(63) Continuation of application No. 12/060,037, filed on Mar. 31, 2008, now Pat. No. 8,083,693.

(60) Provisional application No. 60/909,191, filed on Mar. 30, 2007.

(51) Int. Cl.
*A61B 5/103* (2006.01)
*A61B 5/117* (2006.01)

(52) U.S. Cl.
USPC .............................. 600/594; 600/587; 600/595

(58) Field of Classification Search
USPC .......................................... 600/587, 594, 595
See application file for complete search history.

(56) References Cited

U.S. PATENT DOCUMENTS

| | | |
|---|---|---|
| 3,608,541 A | 9/1971 | Hall |
| 4,007,733 A | 2/1977 | Celeste et al. |
| 4,080,962 A | 3/1978 | Berkeley |
| 4,527,982 A | 7/1985 | Salzman et al. |
| 4,660,829 A | 4/1987 | Whiteneir |
| 4,665,928 A | 5/1987 | Linial et al. |
| 4,730,625 A | 3/1988 | Fraser et al. |
| 4,750,480 A * | 6/1988 | Jenness ........................... 602/19 |
| 4,871,998 A | 10/1989 | Chaillou |
| 5,012,819 A | 5/1991 | Marras et al. |
| 5,143,088 A | 9/1992 | Marras et al. |
| 5,146,929 A | 9/1992 | Sawhill |
| 5,243,998 A | 9/1993 | Silverman et al. |
| 5,398,697 A | 3/1995 | Spielman |
| 5,400,800 A | 3/1995 | Jain et al. |
| 5,402,107 A | 3/1995 | Rencavage |
| 5,425,378 A | 6/1995 | Swezey et al. |
| 5,433,201 A | 7/1995 | Manthey |
| 5,469,861 A | 11/1995 | Piscopo et al. |
| 5,474,083 A | 12/1995 | Church et al. |
| 5,522,401 A | 6/1996 | Brucker |

(Continued)

FOREIGN PATENT DOCUMENTS

| | | |
|---|---|---|
| WO | WO9106082 A1 | 5/1991 |
| WO | 2006/093734 | 9/2006 |

OTHER PUBLICATIONS

"Design Concept of Clothing Recognizing Back Postures" by Mattmann et al., Sep. 4-6, 2006, IEEE-EMBS, pp. 24-27.

(Continued)

*Primary Examiner* — Devin Henson
(74) *Attorney, Agent, or Firm* — Fish & Richardson P.C.

(57) ABSTRACT

In order to monitor an individual's posture, a cable is incorporated within a garment that is configured to be worn on an individual's upper body such that at least a portion of the cable spans an upper back region of the garment. A sensor is configured to monitor tension in the cable and to generate an alert when the tension in the cable exceeds a threshold level.

1 Claim, 12 Drawing Sheets

(56) References Cited

U.S. PATENT DOCUMENTS

| | | | |
|---|---|---|---|
| 5,533,531 A | 7/1996 | Edwards et al. | |
| 5,749,838 A | 5/1998 | Kline | |
| 6,119,516 A * | 9/2000 | Hock | 73/379.01 |
| 6,440,094 B1 | 8/2002 | Maas | |
| 6,673,027 B2 | 1/2004 | Fischer | |
| 7,134,969 B2 * | 11/2006 | Citron et al. | 473/277 |
| 7,842,000 B2 * | 11/2010 | Lai et al. | 602/19 |
| 8,789,293 B2 | 7/2014 | Greene | |
| 2006/0195051 A1 | 8/2006 | Schnapp et al. | |

OTHER PUBLICATIONS

U.S. Non-Final Office Action for U.S. Appl. No. 12/060,037 dated Oct. 19, 2009, 22 pages.
U.S. Final Office Action for U.S. Appl. No. 12/060,037 dated May 20, 2010, 19 pages.
U.S. Non-Final Office Action for U.S. Appl. No. 12/060,037 dated Mar. 11, 2011, 18 pages.
U.S. Notice of Allowance for U.S. Appl. No. 12/060,037 dated Aug. 22, 2011, 12 pages.

* cited by examiner

MONITORING POSTURE

CROSS REFERENCE TO RELATED APPLICATION

This application is a continuation (and claims the benefit of priority under 35 USC 120) of U.S. application Ser. No. 12/060,037, filed Mar. 31, 2008, now allowed, which claims the benefit to U.S. Provisional Patent Application Ser. No. 60/909,191, filed on Mar. 30, 2007 and entitled "System and Method for Controlling Spinal Posture". Both of these prior applications are incorporated by reference in their entirety.

TECHNICAL FIELD

This disclosure relates to monitoring an individual's posture and, in some cases, providing feedback to the individual when the individual is determined to be in a position of poor posture.

BACKGROUND

An individual's posture may depend on the position of the individual's body.

SUMMARY

In one aspect, a system for monitoring an individual's posture includes a garment that is configured to be worn on an individual's upper body. The garment includes a first armpit region and a first shoulder region on a first side of the garment and a second armpit region and a second shoulder region on a second side of the garment that is opposite from the first side of the garment. A channel is incorporated within the garment such that, from the first armpit region of the garment, the channel traverses around the upper back region of the garment to the second shoulder region of the garment, over the second shoulder region of the garment, under the second armpit region of the garment, around the upper back region of the garment to the first shoulder region of the garment, and over the first shoulder region of the garment to the first armpit region of the garment. In addition, a cable is threaded through the channel such that, from the first armpit region of the garment, the cable traverses around the upper back region of the garment to the second shoulder region of the garment, over the second shoulder region of the garment, under the second armpit region of the garment, around the upper back region of the garment to the first shoulder region of the garment, and over the first shoulder region of the garment to the first armpit region of the garment. The system for monitoring an individual's posture also includes a sensor that is configured to monitor tension in the cable and to generate an alert when the tension in the cable exceeds a threshold level.

Implementations may include one or more of the following features. For example, a first end of the cable may be wound around a lockable spool such that, when locked, a length of the cable not wound around the spool remains relatively constant. In addition, the sensor may include a motor that is configured to generate a vibration, a switch that is responsive to a magnetic field and that is configured to inspire the motor to turn on when sufficiently engaged by a magnetic field and to inspire the motor to turn off when not sufficiently engaged by a magnetic field, and a slider that includes a magnet. The slider may be coupled to a second end of the cable and configured to slide in response to changes in tension in the cable. In response to the tension in the cable exceeding the threshold level, the slider may slide to a position in which a magnetic field generated by the magnet engages the switch sufficiently to cause the switch to inspire the motor to turn on. In contrast, in response to the tension in the cable decreasing below the threshold level, the slider may slide away from the position in which the magnetic field generated by the magnet sufficiently engages the switch so as to cause the switch to inspire the motor to turn off.

In some implementations, a housing for the cable may be configured to enable a length of the cable that is incorporated within the garment and not housed within the housing to be fixed. In such implementations, the sensor may be configured to generate an alert, after the length of the cable that is incorporated within the garment and not housed within the housing has been fixed, when the tension in the cable exceeds a threshold level. Additionally or alternatively, the housing may be configured to enable the length of the cable that is incorporated within the garment and not housed within the housing to be adjusted.

The garment may be a shirt or a bra and the sensor may be configured to generate a vibratory alert, an auditory alert, or a visual alert when the tension in the cable exceeds a threshold.

According to another general aspect, an initial tension is established in a cable that is incorporated within a garment that is configured to be worn on an individual's upper body. The garment includes a first armpit region and a first shoulder region on a first side of the garment and a second armpit region and a second shoulder region on a second side of the garment that is opposite from the first side of the garment. The cable is incorporated within the garment such that, from the first armpit region of the garment, the cable traverses around a back of the garment to the second shoulder region of the garment, over the second shoulder region of the garment, under the second armpit region of the garment, around the back of the garment to the first shoulder region of the garment, and over the first shoulder region of the garment to the first armpit region of the garment. The tension in the cable is monitored while the garment is worn on the individual's upper body, and, in response to detecting that the tension in the cable has increased beyond a threshold level, a notification is generated that is intended to alert the individual that the tension in the cable has increased beyond the threshold level.

Implementations may include one or more of the following features. For example, the notification that is intended to alert the individual that the tension in the cable has increased beyond the threshold level may be a vibratory notification, an auditory notification, or a visual notification.

In some implementations, the cable may be coupled to a slider that is configured to slide in response to changes in tension in the cable, and the tension in the cable may be detected to have increased beyond a threshold level by detecting that the slider has slid beyond a threshold position that indicates that the tension in the cable has increased beyond the threshold level.

Additionally or alternatively, the tension in the cable at different periods in time may be recorded and stored such that the stored recorded tensions may be made available to the individual. In some implementations, a visual representation of the stored recorded tensions may be displayed on the display of an electronic device.

According to yet another general aspect, a device for monitoring an individual's posture is manufactured by incorporating a cable into a garment that is configured to be worn on an individual's upper body and that includes a first armpit region and a first shoulder region on a first side of the garment and a second armpit region and a second shoulder region on a second side of the garment that is opposite from the first side of the garment. The cable is incorporated within the garment such that, from the first armpit region of the garment, the cable traverses around a back of the garment to the second shoulder region of the garment, over the second shoulder region of the garment, under the second armpit region of the garment, around the back of the garment to the first shoulder region of the garment, and over the first shoulder region of the garment to the first armpit region of the garment. In addition, some portion of the cable is coupled to a sensor that is configured to detect when tension in the cable exceeds a threshold level and that is configured to generate an alert when tension in the cable exceeds the threshold level.

Implementations may include one or more of the following features. For example, the cable may be incorporated into the garment by first forming a channel in the garment that, from the first armpit region of the garment, traverses around the back of the garment to the second shoulder region of the garment, over the second shoulder region of the garment, under the second armpit region of the garment, around the back of the garment to the first shoulder region of the garment, and over the first shoulder region of the garment to the first armpit region of the garment, and then threading the cable through the channel formed in the garment. Forming the channel in the garment may involve sewing two edges of a piece of fabric to the garment such that the channel is formed between the garment and the piece of fabric sewn to the garment.

In some implementations, the cable may be incorporated into the garment by weaving the cable into the fabric of the garment. The garment may be a shirt or a bra.

According to still another general aspect, a system for monitoring an individual's posture includes a garment configured to be worn on an individual's upper body, a cable incorporated within the garment such that at least a portion of the cable spans an upper back region of the garment, and a sensor that is configured to monitor tension in the cable and to generate an alert when the tension in the cable exceeds a threshold level.

According to an additional general aspect, a system for controlling posture includes a sensor that is structured and arranged to detect whether a user is engaged in a desired posture and a notification system that is structured and arranged to generate an alert in response to receiving an indication from the sensor that the user is no longer engaged in the desired posture.

Implementations may include one or more of the following features. For example, the sensor may includes a cable that may be set to a desired tension level associated with a desired posture, and a housing, including a spool and a wheel actuator, that enables a user to set the desired tension level. In addition, the notification system may be structured and arranged to generate a vibrational alert in response to the sensor detecting an increase in a measured tension level for the cable relative to the desired tension level.

In some implementations, a garment may be structured and arranged to route a portion of the cable between the shoulder and scapulothoracic muscle regions of the garment. Additionally or alternatively, a garment may be structured and arranged to house the notification system.

The various aspects, implementations, and features disclosed may be implemented using, for example, one or more of a method, an apparatus, a system, tool, or processing device for performing a method, a program or other set of instructions, an apparatus that includes a program or a set of instructions, and a computer program embodied in a tangible, computer-readable medium.

The details of one or more implementations are set forth in the accompanying drawings and the description below. Other features will be apparent from the description and the drawings, and the claims.

DETAILED DESCRIPTION

A device for monitoring and promoting improved spinal posture is disclosed. As described in greater detail below, the coupled relationship between an individual's shoulder and spinal muscles may be monitored, and biofeedback (e.g., a vibration) may be provided in response to detecting poor spinal posture. Vibratory biofeedback may be a particularly useful form of biofeedback to provide to the individual because it may alert the individual to the potential that the user has drifted into a position of poor posture without simultaneously broadcasting the alert to others located nearby. A posture stabilizing device such as is disclosed herein may be assembled into (or otherwise incorporated within) a garment (e.g., a shirt or brassiere (bra)) and may provide biofeedback in response to detecting poor posture by the wearer as an instant reminder for the wearer to maintain proper posture. Biofeedback may be provided to the wearer through a biofeedback vibratory system.

Figure 8:
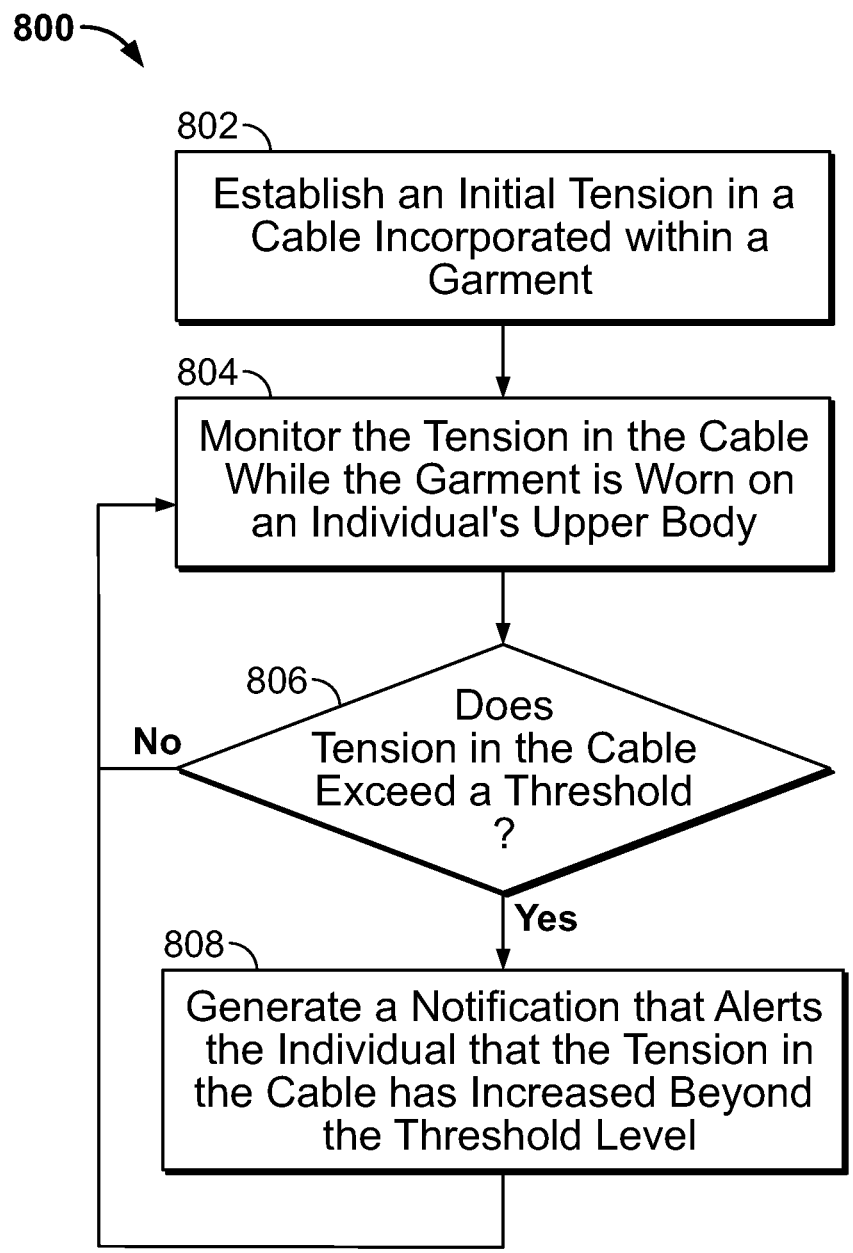
FIG. 8 is a flowchart of a process for monitoring a user's posture.

Specifically, and in one implementation, a monofilament cable is threaded through a channel provided in a shirt (or bra) in a FIG. 8-*like* pattern such that changes in a wearer's upper spinal and shoulder posture result in changes to the tension of the cable. For example, when a wearer of the shirt (or bra) adjusts his/her upper spinal and shoulder posture into an incorrect (or otherwise undesirable) posture, the tension in the cable may increase relative to the tension in the cable when the wearer's upper spinal and shoulder posture is correct. The cable may originate from (or otherwise be coupled to) a housing unit that is incorporated within the shirt (or bra). For example, the housing unit may be sewn in and fitted within a pocket located under an armpit of the shirt (or bra). The housing unit may include an electronics assembly that is configured to detect and respond to changes in the tension of the cable with a vibration. Thus, when tension increases in the cable as a result of a wearer drifting into an incorrect (or otherwise undesirable) posture, the electronics assembly may generate a small vibration that is imparted upon the wearer as a reminder to improve the wearer's posture. When the wearer's posture returns to normal, the tension in the cable may decrease, causing the vibration to cease thereby informing the wearer that the wearer's posture has improved.

Posture

Posture is the position in which a body is positioned in space. Optimal posture allows for precise musculoskeletal balance that provides minimal stress on the joints and organs of the body. The human body is a kinetic chain, and spinal posture is a key component of the overall health of this kinetic chain. Poor posture can have a negative effect on the entire body. An individual's respiratory, digestive, circulatory and, for that matter, entire musculoskeletal system can be compromised when the individual's body is out of balance as a result of poor spinal posture. For instance, poor posture can compromise inflow of air into an individual's lungs secondary to rib cage restrictions.

Figure 1:
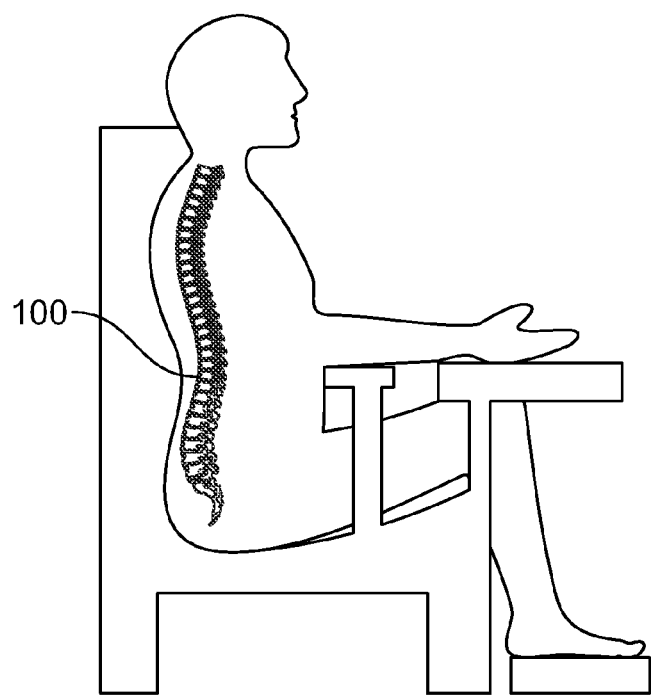
FIG. 1 is a diagram of an individual in a position of good posture.

Posture is the result of many musculoskeletal relationships throughout the body. Posture, thus, becomes a measure of the overall balances and forces on the body exerted by the musculoskeletal system. When an individual's posture is correct, the position of the individual's spine minimizes the pressure on the individual's skeletal system, including the joints of the individual's spine, the individual's intervertebral discs, and the individual's muscles. In spinal vernacular, this ideal position of the spine is termed the "S" shape of the spine, because, as illustrated in FIG. 1, from a side view, the spine 100 looks like an "S" when it is well-balanced.

Figure 2:
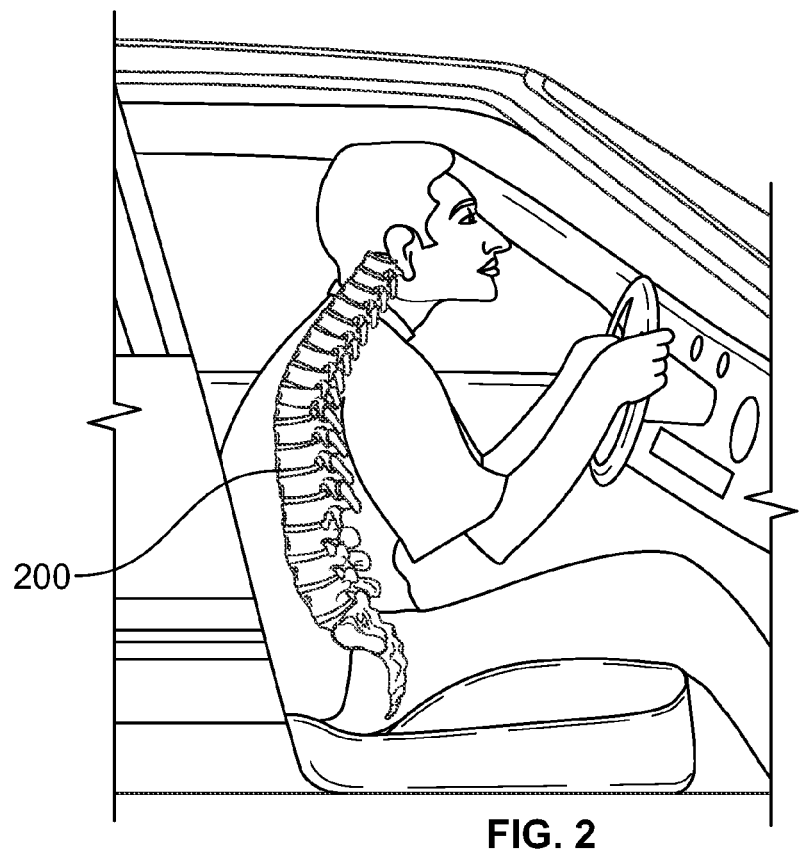
FIG. 2 is a diagram of an individual in a position of poor posture.

Back pain often is caused by bad posture, particularly when an individual sits (or otherwise is oriented) with his/her spine in what is termed a "C" position of the spine. As illustrated in FIG. 2, in this position, the balanced "S-shaped" curve of the individual's spine 200 turns into a "C" shape, causing significant abnormal loads on the individual's spinal musculature and other supporting elements, such as the spinal joints and intervertebral discs. In fact, for every inch an individual's head moves forward, the muscles in the individuals upper back and neck may be subjected to an additional 10 pounds of force. Thus, it is easy to understand, based on these biomechanical principles, that when an individual's spine 200 is in the "C" position, the muscles in the individual's upper and mid low back region have to exert a certain amount of counter pressure to keep the individual's head balanced.

Poor posture or posture in the "C" position also has been shown to have other clinical manifestations, such as headaches, temporomandibular joint disorders, chronic neck pain, shoulder pain, decreased lung capacity and even digestive disorders. In addition, some research suggests that, among older community dwelling men and women, individuals with hyperkyphotic or poor posture have an increased mortality rate relative to individuals with good posture.

Figure 3:
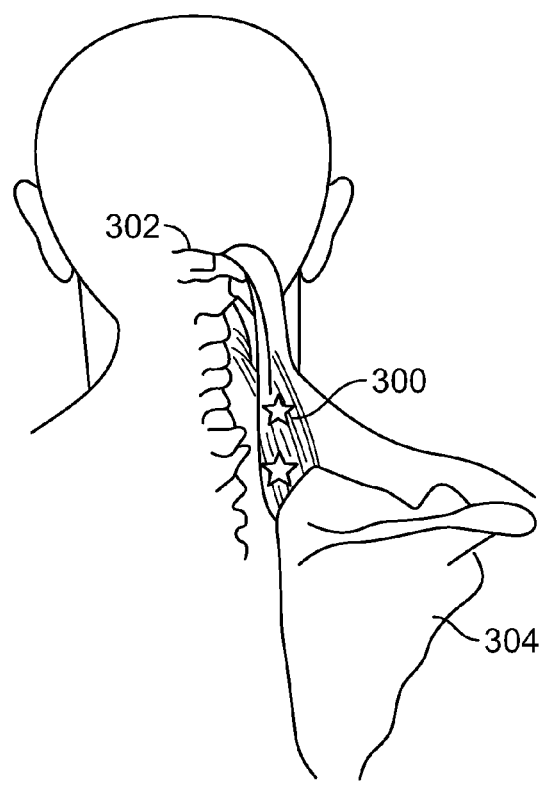
FIG. 3 is a diagram that illustrates the posterior shoulder stabilizers connecting the spine and shoulder through the shoulder blade or the scapula.

The role played by the posterior shoulder stabilizers, also known as the "shoulder blade" muscles, is a neglected component of poor posture. As illustrated in FIG. 3, this group of muscles 300 connects the spine 302 and shoulder through the shoulder blade 304 or the scapula. These upper back muscles 300 have an important function in maintaining upper thoracic posture in what is called both the sagittal plane (side) and the coronal plane (front). Upper spinal posture is a combination of both the direct spinal musculature as well as the very important posterior shoulder musculature, the scapular stabilizers 300. The scapular stabilizers 300 or posterior shoulder muscles play an important role in preventing a multitude of shoulder problems such as rotator cuff tendonitis or impingement syndrome as well as bicipital tendonitis. Therefore, proper upper spinal posture is dependent on a combination of normal functioning posterior shoulder muscles 300 as well as the upper spinal musculature. Thus, upper spinal posture control is based on a "coupled" relationship between the posterior shoulder and upper spinal muscles. This coupled relationship works both ways in that correct upper spinal posture and scapular mechanics are both very important for proper shoulder function.

Monitoring Posture

One difficulty with treating poor posture is that individuals with poor posture often do not realize when they are sitting (or are otherwise oriented) with poor posture, and, while poor posture may not be painful, the long-term consequences of poor posture may be very detrimental. Often, students or desk workers will sit at their desks for prolonged periods of time with poor posture without realizing the extent of their poor posture and the long-term harm it may cause.

Biofeedback may be used to alert a user that the user has drifted into a position of poor posture. Generally speaking, biofeedback is a technique that involves providing an individual with instant feedback about a bodily function or property. For example, an electronic or electromechanical instrument may "feed back" patient information to help to reinforce a certain property. The information may take many forms including, for example, vibratory, auditory, or visual stimuli. As described in greater detail below, an individual's posture may be monitored by monitoring the individual's postural muscle tension and vibratory (and/or other) biofeedback may be provided to the individual when the individual's postural muscle tensions suggests that the individual has slipped into a position of poor posture.

Figure 4A:
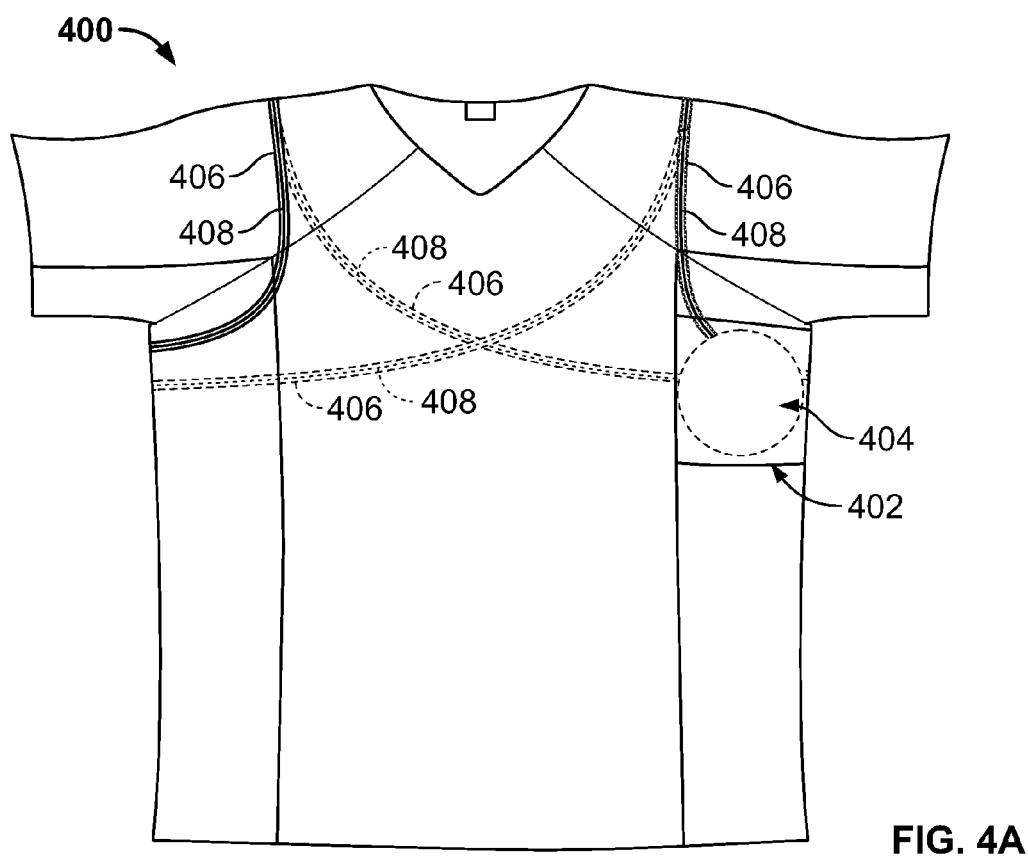
FIGS. 4A-4B are illustrations of different views of a shirt that is equipped to monitor a wearer's posture.
Figure 4B:
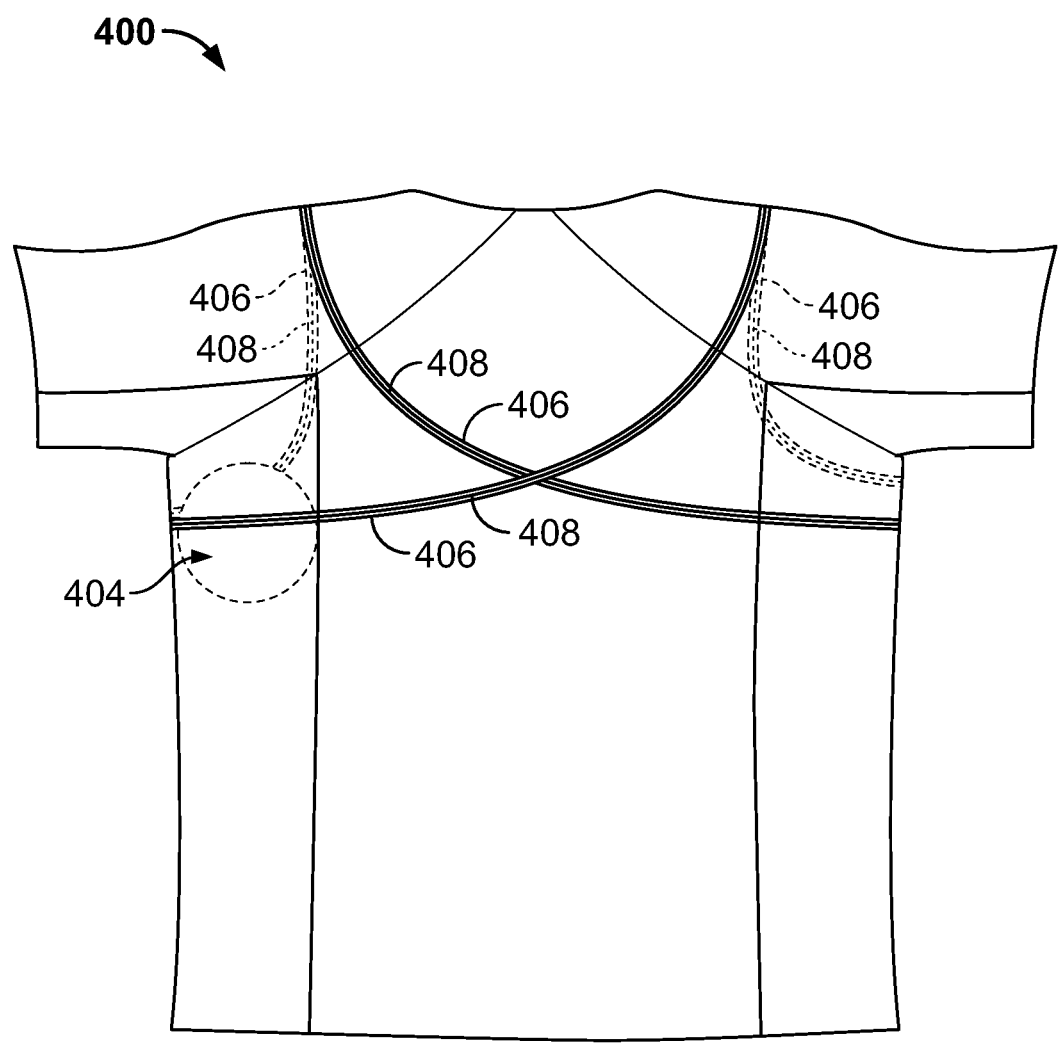

FIG. 4A is a front view of a shirt 400 that is equipped to monitor a wearer's posture and FIG. 4B is a back view of the shirt 400 that is equipped to monitor a wearer's posture. The shirt 400 includes a pocket 402 that houses an electronics assembly 404, an example of which is described in greater detail below in connection with FIGS. 6A-6E. The electronics assembly 404 may be fastened to the shirt 400 by a clip (not shown) (or other fastener) that may be sewn into (or otherwise fastened or adhered to) the shirt 400. When the shirt 400 is worn, the pocket 402 may lie below the wearer's left (or right) armpit or axillary region such that the electronics assembly 404 is positioned in a comfortable and unobtrusive location for the wearer. Of course, the pocket 402 and/or electronics assembly 404 could be located in other positions within the shirt 400. For example, in some implementations, the pocket 402 and/or electronics assembly 404 may be located in or near a collar region of the shirt 400. Additionally or alternatively, the pocket 402 and/or electronics assembly 404 may be located such that the pocket 402 and/or electronics assembly 404 are located near the top of a wearer's shoulder blade when the shirt 400 is worn.

Starting below the left armpit or axillary region of the shirt 400, a channel 406 is woven into the shirt 400 in a FIG. 8-*like* pattern. Referring to FIG. 4A, solid lines are used to illustrate the location of the channel 406 on the front of the shirt 400 and dashed lines are used to illustrate the location of the channel 406 on the back of the shirt 400. Similarly, referring to FIG. 4B, solid lines are used to illustrate the location of the channel 406 on the back of the shirt 400 and dashed lines are used to illustrate the location of the channel 406 on the front of the shirt 400.

From the left armpit or axillary region of the shirt 400, the channel 406 proceeds along the upper back of the shirt 400 into the region of a wearer's right scapula or shoulder blade, drapes over the right shoulder of the shirt 400, and loops under the right armpit or axillary region of the shirt 400. From the right armpit or axillary region of the shirt 400, the channel 406 proceeds along the upper back of the shirt 400 into the region of a wearer's left scapula or shoulder blade, drapes over the left shoulder of the shirt 400, and returns to the left armpit or axillary region of the shirt 400. Numerous different techniques may be employed to weave the channel 406 into the shirt 400. For example, one or more pieces of fabric (or other material), may be sewn (or otherwise fastened or adhered) onto a surface of the shirt 400 to form the channel 406 between the supplemental fabric and the fabric of the shirt 400. In order to best conceal the channel 406, it may be desirable to form the channel 406 on the interior surface of the shirt 400.

A cable 408 having both ends coupled to the electronics assembly 404 is threaded through the channel 406 such that the cable 408 takes on the same FIG. 8-*like* shape as the channel 406. Referring to FIG. 4A, solid lines are used to illustrate the location of the cable 408 on the front of the shirt 400 and dashed lines are used to illustrate the location of the cable 408 on the back of the shirt 400. Similarly, referring to FIG. 4B, solid lines are used to illustrate the location of the cable 408 on the back of the shirt 400 and dashed lines are used to illustrate the location of the cable 408 on the front of the shirt 400.

A cable configured as illustrated in FIGS. 4A-4B may enable the coupled motion of an individual's posterior shoulder and scapulothoracic muscle posture as well as the individual's upper thoracic posture to be monitored. In particular, when an individual regresses into a position of poor posture, and, for example, loses upper thoracic and/or scapular posture, the distance between the individual's shoulders and the distance along the individual's spine may increase. Therefore, when the shirt 400 equipped with the electronics assembly 404, channel 406, and cable 408 is worn, the cable 408 may be stretched and/or the tension in the cable 408 may be increased as the distance between the wearer's shoulders and the distance along the wearer's spine increases as a consequence of wearer slipping into a position of poor posture. The electronics assembly 404 is configured to detect the stretching or increased tension of the cable 408 and to produce a vibratory alarm in response in order to notify the wearer that the wearer potentially has regressed into a position of poor posture.

Of course, the location of the channel 406 and the cable 408 may be adjusted as appropriate for monitoring different positions/postures of a wearer. For example, in some implementations, the location of the channel 406 and the cable 408 may be drawn inward closer to a wearer's neck, while, in other implementations, the location of the channel 406 and the cable 408 may be pushed further outward along a wearer's shoulder. In some implementations, the channel 406 may be secured to the shirt 400 using removable fasteners (e.g., snaps, buttons, hook and loop fastening mechanisms, etc.) that enable a wearer of the shirt to change the location of the channel 406.

The electronics assembly 404 and cable 408 (or a similar variant thereof) also may be incorporated into other garments for the purpose of monitoring wearers' posture. For example, the electronics assembly 404 and cable 408 may be incorporated within a bra (e.g., a "sports bra") in order to monitor a wearer's posture.

Figure 5A:
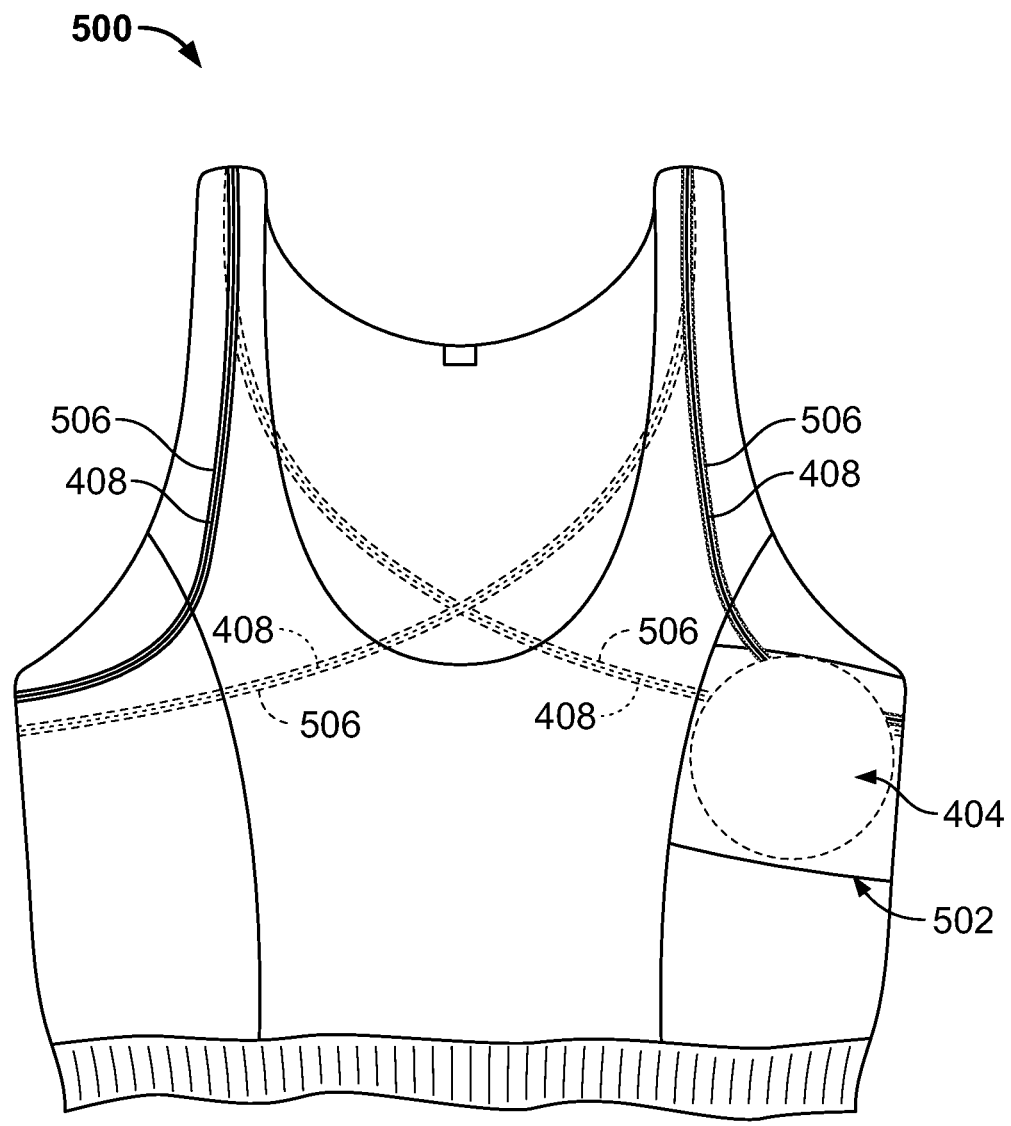
FIGS. 5A-5B are illustrations of different views of a bra that is equipped to monitor a wearer's posture.
Figure 5B:
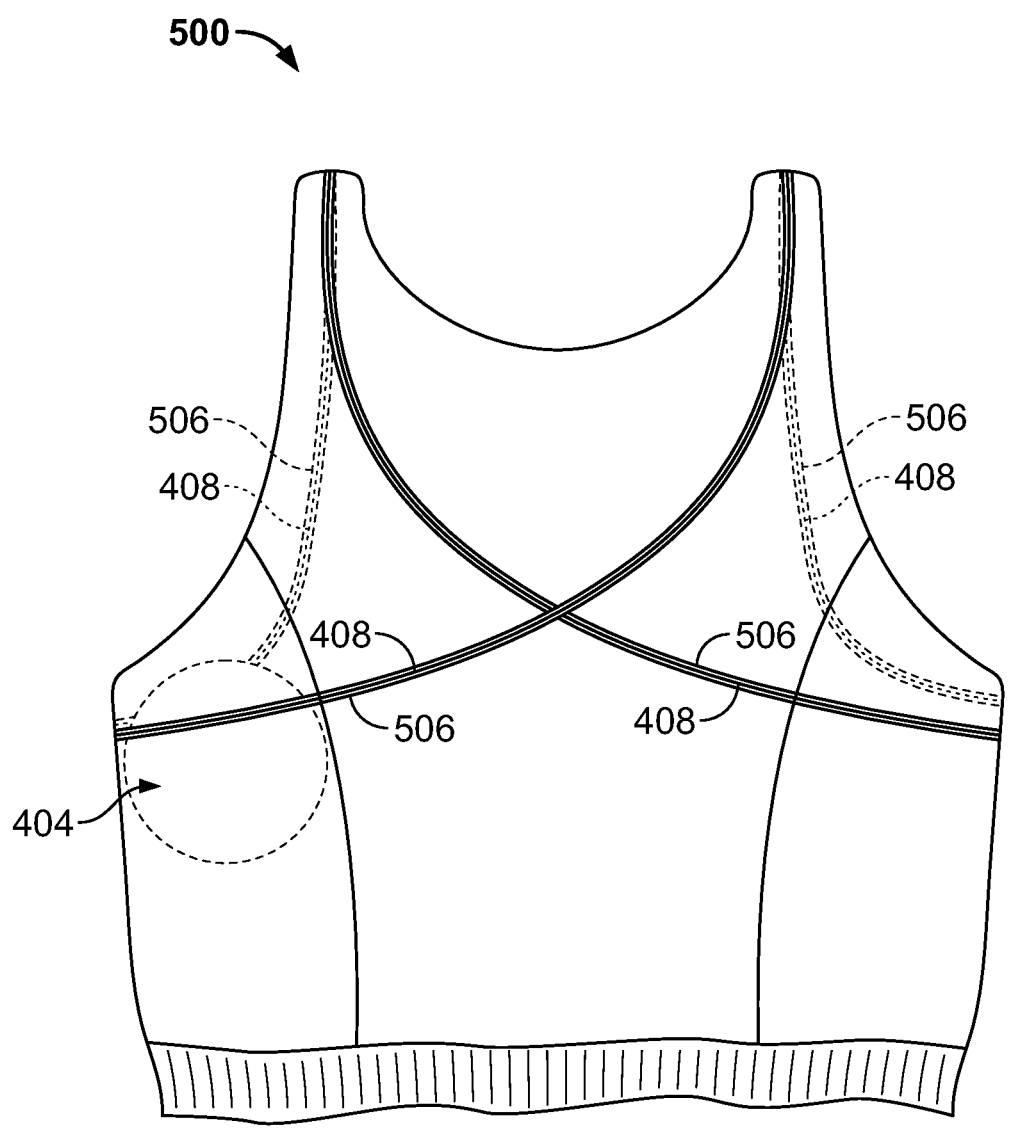

FIG. 5A is a front view of a bra 500 that is equipped to monitor a wearer's posture and FIG. 5B is a back view of the bra 500 that is equipped to monitor a wearer's posture. The bra 500 includes a pocket 502 that houses the electronics assembly 404. The electronics assembly 404 may be fastened to the bra 500 by a clip (not shown) (or other fastener) that may be sewn into (or otherwise fastened or adhered to) the bra 500. When the bra 500 is worn, the pocket 502 may lie below the wearer's left (or right) armpit or axillary region such that the electronics assembly 404 is positioned in a comfortable and unobtrusive location for the wearer. Of course, the pocket 502 and electronics assembly could be located in other positions within the bra 500.

Starting below the left armpit or axillary region of the bra 500, a channel 506 is woven into the bra 500 in a FIG. 8-*like* pattern. Referring to FIG. 5A, solid lines are used to illustrate the location of the channel 506 on the front of the bra 500 and dashed lines are used to illustrate the location of the channel 506 on the back of the bra 500. Similarly, referring to FIG. 5B, solid lines are used to illustrate the location of the channel 506 on the back of the bra 500 and dashed lines are used to illustrate the location of the channel 506 on the front of the bra 500.

From the left armpit or axillary region of the bra 500, the channel 506 proceeds along the upper back of the bra 500 into the region of a wearer's right scapula or shoulder blade, drapes over the right shoulder of the shirt 500, and loops under the right armpit or axillary region of the bra 500. From the right armpit or axillary region of the bra 500, the channel 506 proceeds along the upper back of the bra 500 into the region of a wearer's left scapula or shoulder blade, drapes over the left shoulder of the bra 500, and returns to the left armpit or axillary region of the bra 500. Numerous different techniques may be employed to weave the channel 506 into the bra 500. For example, one or more pieces of fabric (or other material), may be sewn (or otherwise fastened or adhered) onto a surface of the bra 500 to form the channel 506 between the supplemental fabric and the fabric of the bra 500. In order to best conceal the channel 506, it may be desirable to form the channel on the interior surface of the bra 500.

Cable 408, both ends of which are coupled to the electronics assembly 404, is threaded through the channel 506 such that the cable 408 takes on the same FIG. 8-*like* shape as the channel 506. Referring to FIG. 5A, solid lines are used to illustrate the location of the cable 408 on the front of the bra 500 and dashed lines are used to illustrate the location of the cable 408 on the back of the bra 500. Similarly, referring to FIG. 5B, solid lines are used to illustrate the location of the cable 408 on the back of the bra 500 and dashed lines are used to illustrate the location of the cable 408 on the front of the bra 500.

As described above, when an individual regresses into a position of poor posture, the distance between the individual's shoulders and the distance along the individual's spine may increase. Therefore, when the bra 500 equipped with the electronics assembly 404, channel 506, and cable 408 is worn, the cable 408 may be stretched (and the tension in the cable 408 may be increased) as the distance between the wearer's shoulders and the distance along the wearer's spine increases as a consequence of the wearer slipping into a position of poor posture. The electronics assembly 404 is configured to detect the stretching or increased tension of the cable 408 and to produce a vibratory alarm in response in order to notify the wearer that the wearer potentially has regressed into a position of poor posture.

In some implementations, the bra 500 may be worn as an individual garment. Additionally or alternatively, the bra 500 (or a similar halter-top) may be incorporated within another garment to facilitate the monitoring of a wearer's posture. For example, in some implementations, the bra 500 (or a similar halter-top) may be incorporated within a shirt (e.g., a dress or business shirt) to facilitate the monitoring of a wearer's posture.

By way of summary, a device for monitoring an individual's posture may be manufactured or otherwise produced by incorporating a cable into a garment that is configured to be worn on an individual's upper body (e.g., the shirt 400 of FIGS. 4A-4B and/or the bra 500 of FIGS. 5A-5B) such that when a wearer of the garment slips into a position of poor posture, increased tension is applied to the cable and/or the cable is stretched. For example, a cable may be incorporated into a garment such that, from an armpit region of a first side of the garment, the cable traverses around the back of the garment to shoulder region of an opposite side of the garment, over the shoulder region of the opposite side of the garment, under the armpit region of the opposite side of the garment, around the back of the garment to the shoulder region of the first side of the garment, and over the shoulder region of the first side of the garment to the armpit region of the first side of the garment. In some implementations, the cable may be incorporated into the garment by forming a channel in the garment in the desired pattern of the cable and by threading the cable through the channel. In other implementations, the cable may be woven directly into the fabric of the garment.

In addition to incorporating the cable into the garment, a sensor that is configured to detect when the tension in the garment exceeds a threshold value may be affixed to a portion of the cable. In some implementations, the sensor may be configured to generate an alert (e.g., a vibratory, auditory, or visual alert) in response to determining that the tension in the cable exceeds the threshold value.

In some implementations, garments that are configured to monitor a wearer's posture may include or otherwise be composed of "smart fabrics" or "smart fibers" that are capable of detecting the application of tension, strain, and/or pressure to the fabrics/fibers. For example, garments that are configured to monitor a wearer's posture may include or otherwise be composed of "smart fabrics" or "smart fibers" whose electrical resistivity changes in response to the application of tension, strain, and/or pressure to the fabrics/fibers and/or "smart fabrics" or "smart fibers" that are configured to generate vibrations (or other stimuli) in response to the application of tension, strain, and/or pressure. In such implementations, the "smart fabrics" and/or "smart fibers" may be woven into or otherwise incorporated into the garment in a desired pattern (e.g., a pattern similar to the pattern of the channel 406 and cable 408 of FIGS. 4A-4B or the pattern of the channel 506 and cable 408 of FIGS. 5A-5B) such that, when a wearer of the garment drifts into a position of poor posture, tension, strain, and/or pressure is applied to the "smart fabrics" and/or "smart fibers" enabling the "smart fabrics" and/or "smart fibers" to detect that the wearer potentially may have drifted into a position of poor posture.

In implementations in which "smart fabrics" or "smart fibers" whose electrical resistivity changes in response to the application of tension, strain, and/or pressure are incorporated within a garment, the electrical resistivity of the "smart fabrics" or "smart fibers" may be monitored, thereby enabling recordation and later analysis of the wearer's posture over time and/or the triggering of some sort of notification (e.g., a vibratory motor) that the wearer has drifted into a position of poor posture when the applied tension, strain, and/or pressure exceeds a threshold level. In implementations in which "smart fabrics" or "smart fibers" that are configured to generate vibrations (or other stimuli) in response to the application of tension, strain, and/or pressure are incorporated within a garment, the "smart fabrics" or "smart fibers" may generate vibrations (or other stimuli) when a wearer slips into a position of poor posture because of the added tension, strain, and/or pressure applied to the "smart fabrics" or "smart fibers" when the user drifts into a position of poor posture.

Figure 6A:
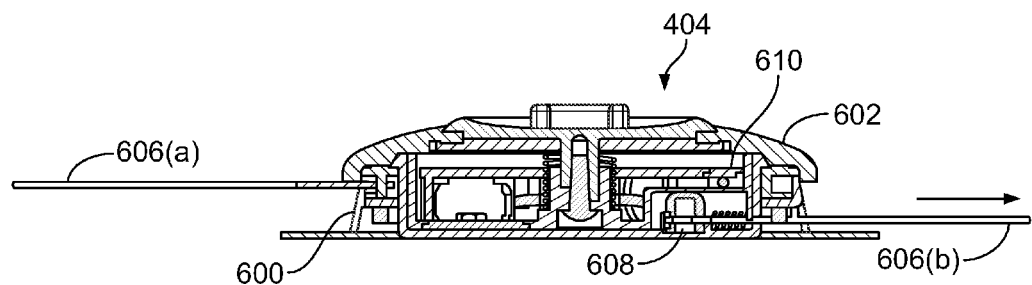
FIGS. 6A-6E are illustrations of different views of an example of an electronics assembly that is configured to monitor an individual's posture.
Figure 6B:
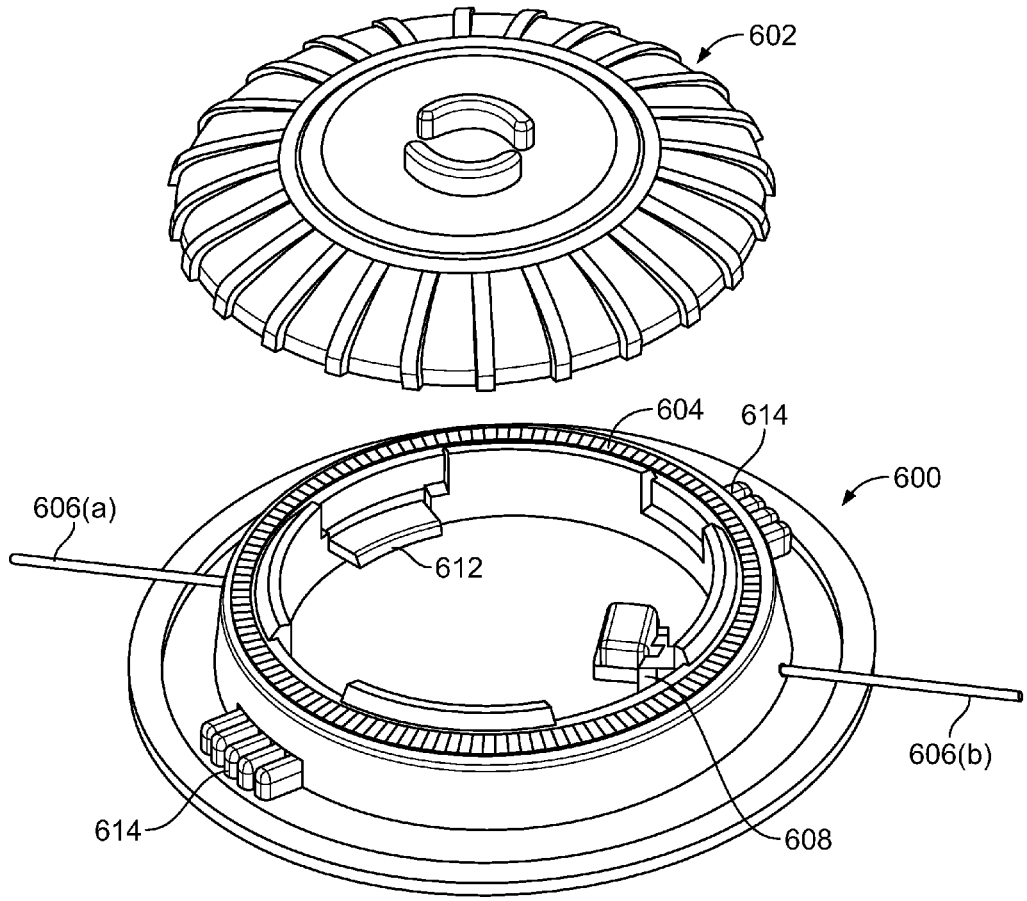
Figure 6C:
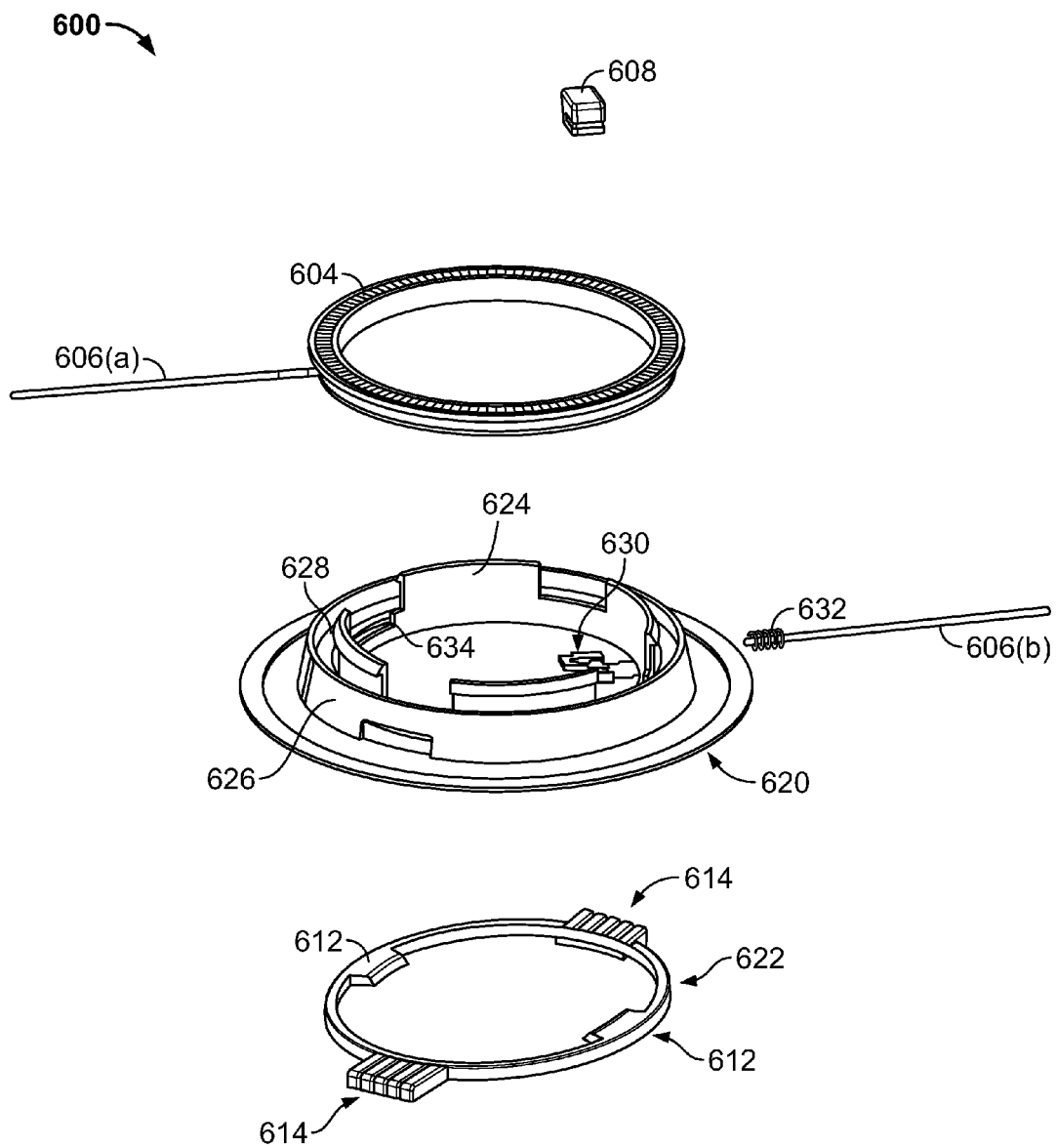
Figure 6D:
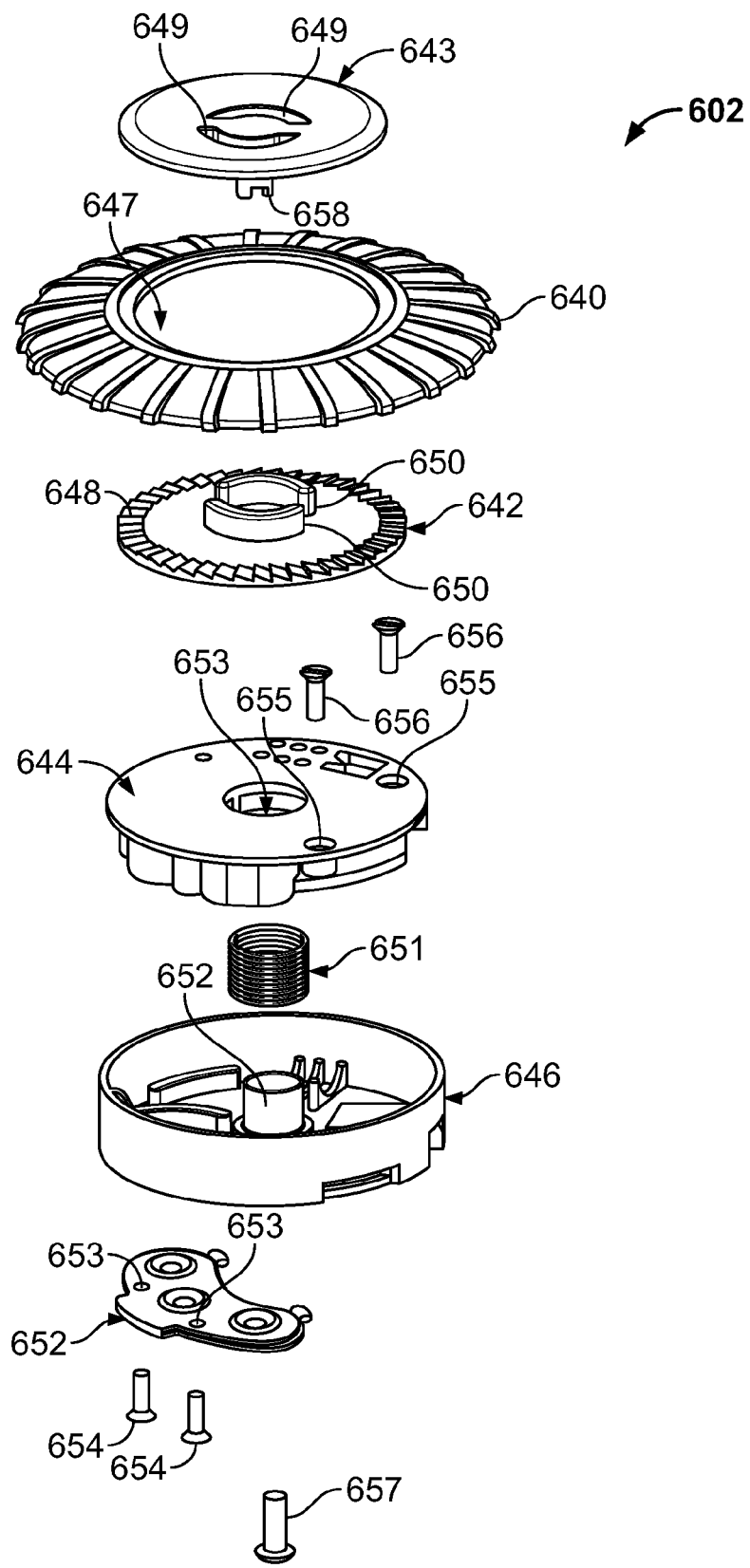
Figure 6E:
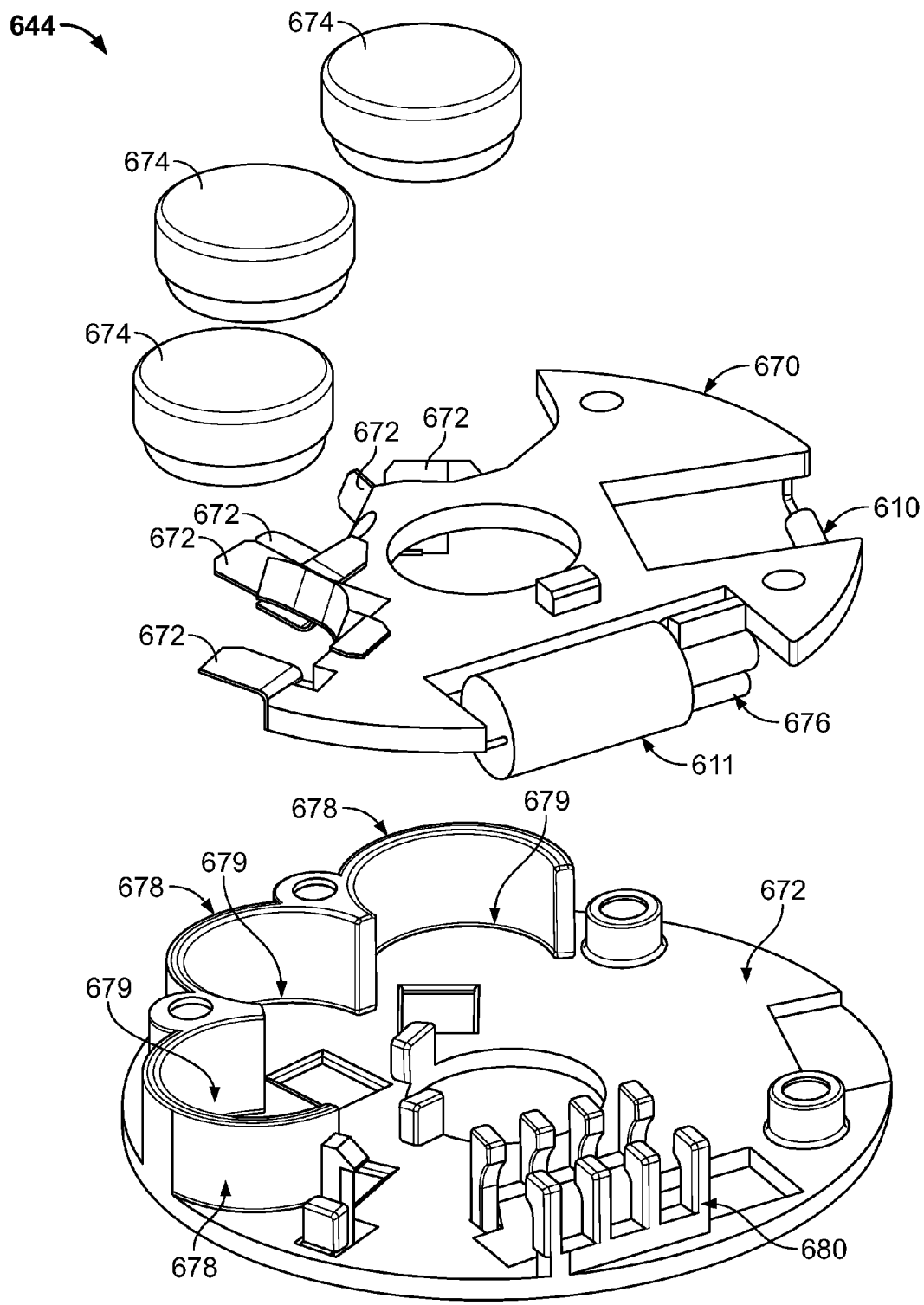

FIGS. 6A-6E are illustrations of different views of the example of the electronics assembly 404. In particular, FIG. 6A is a cross-sectional view of the electronics assembly 404. FIG. 6B is an exploded view of the electronics assembly 404 showing a shirt clip assembly 600 that can be sewn into (or otherwise attached to) a garment (e.g., the shirt 400 of FIGS. 4A-4B and/or the bra 500 of FIGS. 5A-5B) and that is configured to receive and secure a printed circuit board (PCB) housing 602. FIG. 6C is an exploded view of the shirt clip assembly 600, FIG. 6D is an exploded view of the PCB housing 602, and FIG. 6E is an exploded view of a PCB assembly 644 of the PCB housing 602.

Referring to FIGS. 6A-6B, the electronics assembly 404 includes a shirt clip assembly 600 that is configured to receive and secure a PCB assembly 602. As discussed above in connection with FIGS. 4A-4B and 5A-5B, the shirt clip assembly 600 may be sewn into (or otherwise attached to) a garment (e.g., the shirt 400 of FIGS. 4A-4B and/or the bra 500 of FIGS. 5A-5B). In addition, the shirt clip assembly 600 is configured to receive and secure the PCB assembly 602. The shirt clip assembly 600 also houses a spool 604 around which a cable 606 is wound. An originating end 606(*a*) of the cable 606 emerges from the spool 604, and, as described above in connection with FIGS. 4A-4B and 5A-5B, the cable 606 may be threaded through a channel that is woven into a garment in a FIG. 8-*like* pattern such that a terminating end 606(*b*) is coupled to a slider 608 that includes a magnet. The slider 608 may be configured to slide back and forth linearly in a radial direction relative to the shirt clip assembly 600.

The PCB assembly 602 includes a reed switch 610 (e.g., Hamlin Electronics MITI-3V1 6-12.5) that, when closed, allows electric current to be sent to a motor 611 (see FIG. 6E) which causes the motor 611 to run and, as described more fully below, the electronics assembly 404 to vibrate. The shirt clip assembly 600 is configured to receive the PCB housing 602 such that when the slider 608 slides in an outward radial direction from the slider's rest position, the magnetic field generated by the magnet within the slider 608 engages the reed switch 610 causing the reed switch 610 to close. In addition, the shirt clip assembly 600 includes clips 612 that are configured to engage and secure the PCB assembly 602 within the shirt clip assembly 600. Trigger buttons 614 control the clips 612 such that when the trigger buttons 614 are depressed, the clips 612 disengage the PCB assembly 602 allowing the PCB assembly 602 to be removed from the shirt clip assembly 600.

When the PCB assembly 602 is secured within the shirt clip assembly 600, a locking mechanism may lock the spool 604 in one direction such that the cable 606 may be retracted but additional cable 606 may not be released. Consequently, the application of tension to the cable 606 causes the slider 608 to slide in an outward radial direction. As the slider 608 slides in the outward radial direction, the magnetic field generated by the magnet engages the reed switch 610, causing the reed switch 610 to close. In turn, the closing of the reed switch 610 allows electric current to be sent to the motor 611, resulting in the turning on of the motor 611, which causes the electronics assembly 404 to vibrate. In some implementations, an eccentric (e.g., off balance) weight may be located at the end of the motor shaft such that the rotation of the eccentric weight causes a vibration. When the tension is removed from the cable 606, the slider 608 slides in an inward radial direction returning to its rest position and the magnetic field generated by the magnet in the slider 608 disengages the reed switch 610 causing the reed switch 610 to open. As a result, the flow of electric current to the motor 611 stops, the motor 611 shuts off and the vibration ceases.

When the electronics assembly 404 and cable 606 are incorporated within a garment such as as described in connection with the shirt 400 of FIGS. 4A-4B and bra 500 of FIGS. 5A-5B, tension may be applied to the cable 606 when a wearer of the garment slips into a position of poor posture, thereby triggering the motor 611 to generate a vibration that serves to alert the wearer that the wearer may have slipped into a position of poor posture. When the wearer returns to a position of better posture, the tension is removed from the cable 606 and the motor 611 stops generating the vibration.

Referring to FIG. 6C, the shirt clip assembly 600 is described in greater detail. As illustrated in FIG. 6C, the shirt clip assembly 600 includes a shirt clip 620, a PCB board housing securing mechanism 622 and a spool 604 that houses a cable 606. The shirt clip 620 includes two concentric walls, an interior wall 624 and an exterior wall 626 which define a channel 628 that is configured to receive the spool 604. In addition, a groove 630 formed in the shirt clip 620 is configured to receive the slider 608 so as to enable the slider 608 to slide back and forth in a linear radial direction. The slider 608 is configured to be coupled to the terminating end 606(b) of the cable 606. When the shirt clip assembly 600 is fully assembled, the terminating end 606(b) of the cable 606 is threaded through a compression spring 632 that is positioned between the slider 608 and the interior wall 624 of the shirt clip 620 to help return the slider 608 to its rest position when tension is removed from the cable 606. When fully assembled, the PCB securing mechanism 622 rests beneath the shirt clip 626, and openings 634 formed in the interior wall 624 of the shirt clip allow the clips 612 of the PCB securing mechanism 622 to engage and secure the PCB housing 602.

Referring to FIG. 6D, the PCB housing 602 is described in greater detail. As illustrated in FIG. 6D, the PCB housing 602 includes a wheel 640, a button 642, a top cap 643, a PCB assembly 644, and a PCB casing 646. An opening 647 in the wheel 640 is configured to receive the top cap 643. When assembled, the wheel rests atop the button 642 such that teeth on the button 642 engage corresponding teeth (not shown) on the underside of the wheel 640, allowing the wheel 640 to be turned in one direction but not the other. Slots 649 in the top cap 643 are configured to receive vertical extensions 650 that extend upward from the button 642, and compression spring 651, which rests around a column 652 that extends from the PCB casing 646 and which extends through an opening 653 defined in the PCB assembly 644, is configured to apply a force on the button 642 such that the vertical extensions 650 from the button 642 are maintained within the slots 649 in the top cap 643. When the vertical extensions 650 from the button 642 are depressed, the compression spring 651 compresses, causing the teeth 648 on the button 642 to disengage the corresponding teeth (not shown) on the wheel 640 allowing the wheel 640 to be turned freely in both directions.

An opening (not shown) in the PCB casing 646 is configured to receive a battery door 652 which provides access to one or more batteries (not shown) that are used to provide power to the motor. Holes 653 in the battery door 652 are configured to receive screws 654 that are configured to engage threaded holes (not shown) in the PCB assembly 644 thereby securing the battery door to the PCB casing 646 and securing the PCB casing 646 to the PCB assembly 644. Holes 655 in the PCB assembly 644 are configured to receive screws 656 that are configured to engage threaded holes (not shown) in the PCB casing 646 thereby enabling the PCB assembly 644 to be secured to the PCB casing 646. Screw 657 is configured to be threaded through column 652 of the PCB casing 646 and to engage jaws 658 which extend from the top cap 643 enabling the entire PCB housing 602 to be secured together.

Referring to FIG. 6E, the PCB assembly 644 is described in greater detail. As illustrated in FIG. 6E, the PCB assembly 644 includes a PCB 670 and a PCB casing 672. The PCB 670 includes battery contacts 672 for engaging batteries 674 (e.g., LR44 batteries, 1.5 v). When the reed switch 610 is closed by the moving of the magnet in the slider 608, current is allowed to flow from the batteries 674 through circuitry (not shown) on the PCB 670 to drive the motor 611 (e.g., Namiki 6CH-1201WL-0; MAX1749 Vibrator Motor Driver SOT23-5 package). An eccentric (e.g., off balance) weight 676 is attached to an end of the motor 611 shaft. When the motor 611 is driven, the eccentric weight 676 rotates thereby generating a vibration. Serpentine walls 678 formed on the PCB casing 672 define wells 679 that are configured to receive the batteries 674. In addition, jaws 680 formed on the PCB casing 672 are configured to receive and secure the motor 611.

Garments that are equipped to monitor a wearer's posture and to provide biofeedback when the wearer drifts into a position of poor posture, such as the shirt 400 of FIGS. 4A-4B and the bra 500 of FIGS. 5A-5B, may be worn just like other normal garments.

Figure 7A:
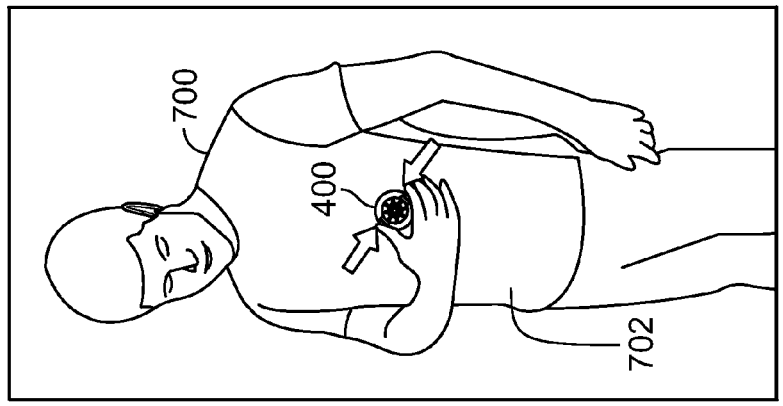
FIGS. 7A-7D are illustrations of an individual wearing a garment that is equipped to monitor the individual's posture and to provide biofeedback when the individual slips into a position of poor posture.

FIGS. 7A-7D are illustrations of an individual 700 wearing a garment 702 (e.g., a shirt) that is equipped to monitor the individual's posture and to provide biofeedback when the individual 700 slips into a position of poor posture. As illustrated in FIG. 7A, the individual 700 may adjust the tension in the cable (not shown) by rotating the wheel 640 of the electronics assembly 404. The wheel 640 interfaces with the spool 604 that houses the cable. The wheel 640 may be allowed to rotate in one direction while being prohibited from rotating in the other direction to ensure that the cable remains taut and does not come loose. To release tension in the cable, the button 642 may be depressed allowing the spool 604 to spin freely in both directions.

Figure 7B:
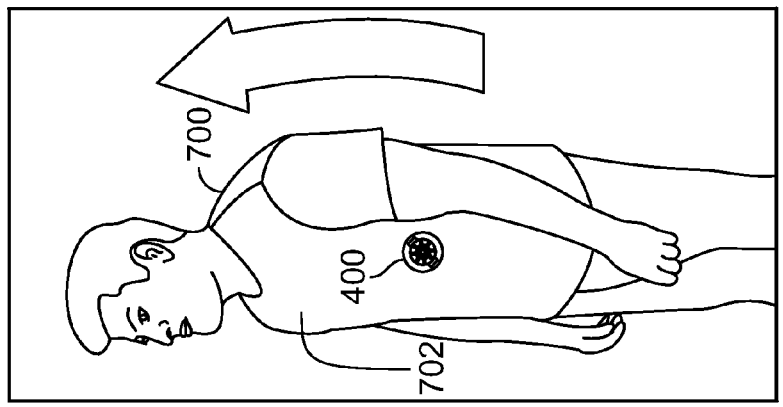

After the individual 700 dons the garment 702, the individual 700 may adjust his/her body into a position of good posture and then set an appropriate tension in the cable. Referring to FIG. 7B, the individual 700 may position him/herself in a position of good posture by placing his/her shoulders against a flat wall while donning the garment 700. Once the individual's shoulders are against the wall, the wheel 640 may be rotated and the tension in the cable may be set just below the threshold that causes the motor to fire a vibration. When the individual 700 is in a position of good posture, the cable may be arranged such that it traverses the shortest possible distance through the channel in the garment 702. The configuration of the cable in this position may be referenced as the "home" position.

Figure 7C:
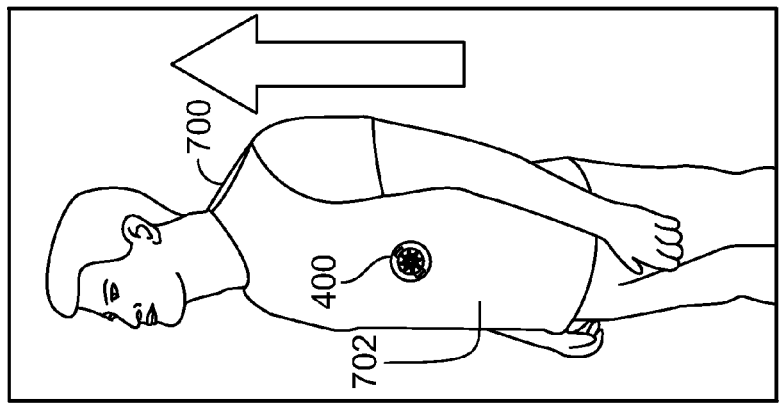

Referring to FIG. 7C, if the individual 700 slouches into poor posture, the cable is stretched as a consequence of the distance between the individual's shoulder and spine increasing. This stretching of the cable allows the individual's improper posture to be sensed, which, in turn, triggers vibratory biofeedback that alarms the individual 700 that the individual 700 has slipped into a position of poor posture.

Figure 7D:
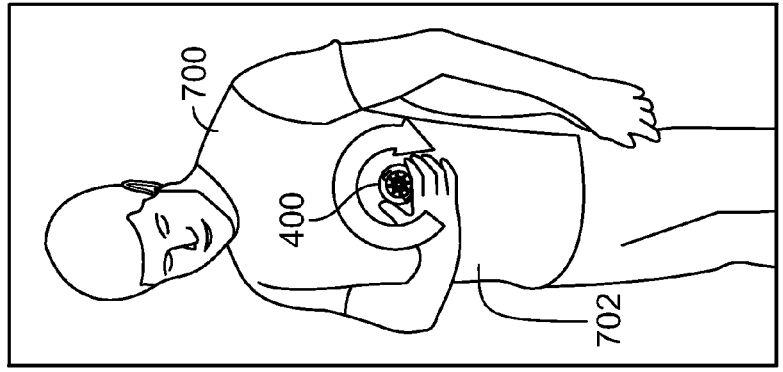

Referring to FIG. 7D, individual 700 may simply remove the electronics assembly 404 from the garment 700 by depressing the two peripheral trigger buttons 614. This simple removal of the electronics assembly 404 may allow the garment to be washed and dried in typical fashion. In addition, this simple remove of the electronics assembly 404 may enable the electronics assembly to be transferred from one garment to another garment based on the needs and desires of the user. Hence, one removable electronics assembly 404 may be placed in different garments depending on the personal needs of the individual 700.

Garments that are equipped to monitor a wearer's posture and to provide biofeedback when the wearer slips into a position of poor posture, such as the shirt 400 of FIGS. 4A-4B and the bra 500 of FIGS. 5A-5B, may be particularly useful in the context of exercise or athletics. For example, in order to prevent injury while an athlete is lifting weights (or engaged in another exercise), it may be very important that the athlete maintain proper posture throughout a weight lifting (or other) exercise. Thus, when an athlete is wearing a garment that provides biofeedback when the athlete slips into a position of poor posture, the athlete may be able to correct his/her posture when he/she slips into a position of poor posture quickly before injury occurs.

In addition, in one implementation, the garment may be associated with a particular sport or other athletic activity. For example, a baseball coach may use a garment configured to assist with developing a particular baseball stance (e.g., fielding or batting) and/or a golf professional may use a garment configured to assist with developing a proper swing. Before practicing a particular activity (e.g., before taking batting practice or swinging a golf club), a coach or other instructor may configure the garment to measure whether the athlete adopts an undesired stance or motion during the activity. As a result, if the sensor detects that the desired thresholds are being exceeded (e.g., the tension across one or more monitored spans exceeds a specified tension), a notification (vibration) may be generated, notifying the athlete that the athlete's body is not positioned correctly. This may enable the athlete to develop the muscle memory required to improve the athlete's performance in the activity (e.g., improve the athlete's baseball or golf swing).

FIG. 8 is a flowchart 800 of a process for monitoring a user's posture. The process begins by establishing an initial tension in a cable that is incorporated within a garment such as as described in connection with the shirt 400 of FIGS. 4A-4B and/or the bra 500 of FIGS. 5A-5B (802). The initial tension may be established while the garment is worn by an individual and while the individual is in a position of good posture (or an otherwise preferred position) such that when the user strays from the position of good posture (or the otherwise preferred position), the tension in the cable is increased and/or the cable is stretched. In some instances, the initial tension in the cable may be appropriate and therefore does not need to be changed. In other instances the initial tension in the cable may need to be adjusted by, for example, extending additional cable or retracting excess cable.

After the initial tension in the cable is established, the tension in the cable is monitored while the garment is worn on the individual's upper body (804) to detect when the tension in the cable exceeds a threshold value that indicates that the individual has slipped into a position of poor posture (806). When the tension in the cable is determined to exceed the threshold value, a notification is generated to alert the individual that the tension in the cable exceeds the threshold level (808) indicating that the individual may have slipped into a position of poor posture. For example, in some implementations, a vibration may be generated in response to determining that the tension in the cable exceeds a threshold value to alert the individual that the individual may have slipped into a position of poor posture. Additionally or alternatively, an auditory alert (e.g., a beep or chime, a pattern of beeps and/or chimes, or a spoken message) and/or a visual alert (e.g., a flashing light) may be generated when the tension in the cable is determined to exceed the threshold value.

As described above in connection with FIGS. 6A-6E, in some implementations, one end of the cable may be coupled to a slider that is configured to slide back and forth in a linear fashion in response to changes in the tension in the cable. In such implementations, the back and forth sliding of the slider may be considered to amount to monitoring the tension in the cable, and the tension in the cable may be determined to exceed a threshold level when the slider slides beyond a predetermined position. In additional or alternative implementations, the cable may not be coupled to a slider. Rather, in such implementations, other sensors that are configured to monitor the tension in the cable may be employed (be they sensors that are directly coupled to the cable or sensors that are not directly coupled to the cable but that nevertheless are capable of monitoring tension in the cable.)

In some implementations, electronic equipment including, for example, a tension sensor, a processor, a memory or other storage component, and/or a data recorder may be used to monitor and record the tension in the cable at various points in time. For example, the tension in the cable may be recorded periodically (e.g., once every minute or once every ten minutes) or the tension may be recorded in response to one or more triggering events (e.g., a determination that the tension in the cable exceeds the threshold level). In some implementations, the number of times the tension in the cable is determined to exceed the threshold level may be recorded. After the tension in cable is recorded, it may be uploaded to a computer or otherwise be made available to the individual or a healthcare professional via an electronic device. For example, a wired or wireless connection may be established between the electronic equipment and a computer or other electronic device enabling the recorded tension information to be uploaded to the computer or other electronic device. In some implementations, the recorded tension information may be uploaded to a portable electronic device (e.g., a portable media device, a portable digital assistant, a smart phone, etc.) such that the recorded tension information may be easily reviewed (and/or transported). In addition, in some implementations, a garment that is configured to monitor a user's posture may be equipped to provide a convenient location to store such a portable electronic device while the garment is worn so that recorded tension information may be uploaded to the portable electronic device in real-time while the garment is worn. In some implementations, recorded tension information may be stored on a removable storage medium and transferred to a remote computer or other electronic device. In addition, in one configuration, the notification system may be disabled to perceive whether a wearer pursues proper poster without receiving instantaneous biofeedback (using the recorded tension information).

Figure 9:
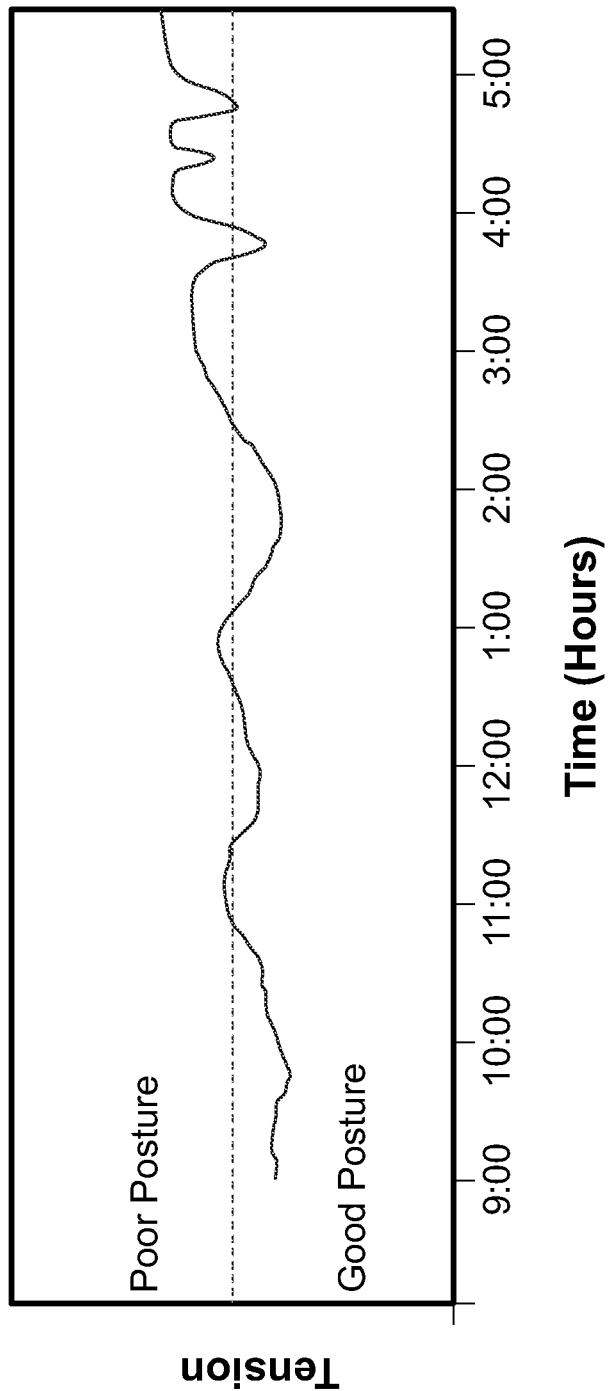
FIG. 9 is an example of a graph that is reflective of an individual's posture over time.

In some implementations, after recorded tension information has been uploaded to a computer or other electronic device, convenient representations of the recorded tension information may be made available for review by the individual or a healthcare professional. For instance, a graph or similar visual representation of the recorded tension information may be generated and displayed thereby enabling the individual or a healthcare professional to review the recorded tension information, for example, in order to identify trends in the user's posture over time. For example, referring to FIG. 9, a graph of the tension in the cable over the course of an eight-hour workday may be generated from the recorded tension information to enable the individual or a healthcare professional to track the individual's posture through the day. As illustrated in FIG. 9, such a graph may indicate that the individual's posture grew progressively worse over the course of the day as the individual grew tired. Armed with this knowledge, the individual may make a more concerted effort in the future to maintain good posture throughout the course of the day, even as the individual grows weary toward the end of the day. In some implementations, the tension in the cable may be monitored and/or recorded without providing instantaneous biofeedback to the individual, but rather allowing the individual to subsequently review the recorded tension information for a period of time. Such implementations may be particularly useful when the individual desires to monitor his/her posture during an activity (e.g., sleeping) but does not wish to be disturbed during the activity.

The systems and techniques described above are not limited to any configuration. In addition, the methods and processes described may be implemented as computer programs that are executed on programmable devices comprising at least a processor and a data storage system. Such computer programs typically will be stored on computer-readable storage media or devices (e.g., CD-Rom, RAM, or magnetic disk). When read into a processor and executed, the instructions of the programs may cause a device to carry out the various operations described above.

A number of implementations have been described. Nevertheless, it will be understood that various modifications and implementations may be made. For example, additional configurations may be applied to a garment to enable the garment to monitor and detect postural changes and to generate biofeedback (e.g., a vibratory, auditory, and/or visual alarm) in response to sensing that a wearer of the garment has drifted into a position of poor (or otherwise undesirable) posture. Furthermore, useful results may be achieved if steps of the disclosed techniques are performed in a different order and/or if components in the disclosed systems are combined in a different manner and/or replaced or supplemented by other components. Accordingly, other implementations are within the scope of the following claims.

What is claimed is:

1. A system for monitoring an individual's posture, the system comprising:
  a garment that is configured to be worn on an individual's upper body and that includes a first armpit region and a first shoulder region on a first side of the garment and a second armpit region and a second shoulder region on a second side of the garment, wherein the first side of the garment is opposite from the second side of the garment;
  a channel that is incorporated within the garment such that, from the first armpit region of the garment, the channel traverses around the upper back region of the garment to the second shoulder region of the garment, over the second shoulder region of the garment, under the second armpit region of the garment, around the upper back region of the garment to the first shoulder region of the garment, and over the first shoulder region of the garment to the first armpit region of the garment;
  a cable that is threaded through the channel such that, from the first armpit region of the garment, the cable traverses around the upper back region of the garment to the second shoulder region of the garment, over the second shoulder region of the garment, under the second armpit region of the garment, around the upper back region of the garment to the first shoulder region of the garment, and over the first shoulder region of the garment to the first armpit region of the garment; and
  a sensor that is configured to:
  deploy in a loosened state for the individual to fit the garment,
  enable the individual to increase the tension in the cable to a comfort level that also maintains a desired posture,
  set a threshold level of tension in the cable;
  monitor tension in the cable and to generate an alert when the tension in the cable exceeds the threshold level.

* * * * *